US00PP18153P2

(12) United States Plant Patent
Tsukahara

(10) Patent No.: US PP18,153 P2
(45) Date of Patent: Oct. 30, 2007

(54) ***PETUNIA* PLANT NAMED 'BLUE FRILL PINK'**

(50) Latin Name: *Petunia×hybrida*
Varietal Denomination: Blue Frill Pink

(75) Inventor: Jun Tsukahara, Yame (JP)

(73) Assignee: Dai-Ichi Seed Co., Ltd., Tokyo (JP)

( * ) Notice: Subject to any disclaimer, the term of this patent is extended or adjusted under 35 U.S.C. 154(b) by 0 days.

(21) Appl. No.: 11/444,194

(22) Filed: May 31, 2006

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Petunia* plant named 'Blue Frill Pink', characterized by its outwardly spreading growth habit; freely branching and flowering plant habit; rapid growth rate; and relatively small bright pink-colored flowers with distinct frilled edges.

1 Drawing Sheet

Botanical designation: *Petunia×hybrida.*
Cultivar denomination: 'Blue Frill Pink'.

BACKGROUND OF THE INVENTION

The present invention relates to a new and distinct cultivar of *Petunia,* botanically known as *Petunia×hybrida* and hereinafter referred to by the name 'Blue Frill Pink'.

The new *Petunia* is a product of a planned breeding program conducted by the Inventor in Shizuocka Prefecture, Japan. The objective of the breeding program is to create new *Petunia* cultivars with attractive foliage shape and coloration.

The new *Petunia* originated from a cross-pollination made by the Inventor in April, 1999 in Shizuocka Prefecture, Japan of the *Petunia×hybrida* cultivar Bluette Purple, not patented, as the female, or seed, parent with an unidentified proprietary selection of *Petunia×hybrida,* not patented, as the male, or pollen, parent. The new *Petunia* was discovered and selected by the Inventor as a single flowering plant within the progeny of the stated cross-pollination in a controlled environment in Shizuoka Prefecture, Japan in July, 2000.

Asexual reproduction of the new *Petunia* by terminal cuttings in a controlled environment in Shizuoka Prefecture, Japan since July, 2000, has shown that the unique features of this new *Petunia* are stable and reproduced true to type in successive generations.

SUMMARY OF THE INVENTION

The cultivar Blue Frill Pink has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Blue Frill Pink'. These characteristics in combination distinguish 'Blue Frill Pink' as a new and distinct cultivar of *Petunia:*

1. Outwardly spreading growth habit.
2. Freely branching and flowering plant habit.
3. Rapid growth rate.
4. Relatively small bright pink-colored flowers with distinct frilled edges.

Plants of the new *Petunia* can be compared to plants of the female parent, the cultivar Bluette Purple. Plants of the new *Petunia* differ from plants of the cultivar Bluette Purple in the following characteristics:

1. Plants of the new *Petunia* are more upright and have thinner stems than plants of the cultivar Bluette Purple.
2. Plants of the new *Petunia* have paler green-colored and thinner leaves than plants of the cultivar Bluette Purple.
3. Plants of the new *Petunia* are more fragrant than plants of the cultivar Bluette Purple.

Plants of the new *Petunia* can be compared to plants of the male parent, the unidentified selection of *Petunia×hybrida.* Plants of the new *Petunia* differ primarily from plants of the male parent selection in the following characteristics:

1. Plants of the new *Petunia* are more freely branching and more uniform than plants of the male parent selection.
2. Plants of the new *Petunia* has more intense pink-colored flowers than plants of the male parent selection.

Plants of the new *Petunia* can also be compared to plants of the cultivar Bluette White, disclosed in U.S. Plant Pat. No. 15,492. In side-by-side comparisons conducted in Shizuoka Prefecture, Japan, plants of the new *Petunia* and the cultivar Bluette White differed primarily in flower color as plants of the cultivar Bluette White had white-colored flowers.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia*.

The photograph at the bottom of the sheet comprises a side perspective view of a typical flowering plant of 'Blue Frill Pink' grown in a container.

The photograph at the top of the sheet comprises a close-up of typical flowers of 'Blue Frill Pink'.

DETAILED BOTANICAL DESCRIPTION

The photographs and following observations, measurements and values describe plants grown in Lompoc, Calif., under commercial practice during the winter and spring in a polycarbonate-covered greenhouse with day temperatures ranging from 21° C. to 24° C., night temperatures ranging from 16° C. to 18° C., and light levels ranging from about 5,000 to 9,000 foot candles. Plants were grown for about eleven weeks with one plant per 10-cm container. In the following description, color references are made to The Royal Horticultural Society Colour Chart, 1995 Edition, except where general terms of ordinary dictionary significance are used.

Botanical classification: *Petunia×hybrida* cultivar Blue Frill Pink.

Parentage:

*Female, or seed, parent.*—*Petunia×hybrida* cultivar Bluette Purple, not patented.

*Male, or pollen, parent.*—Unidentified selection of *Petunia×hybrida,* not patented.

Propagation:

*Type.*—By terminal cuttings.

*Time to initiate roots, summer.*—About one week at temperatures of 30° C.

*Time to initiate roots, winter.*—About two weeks at temperatures of 15° C.

*Time to produce a rooted young plant, summer.*—About 20 days at temperatures of 30° C.

*Time to produce a rooted young plant, winter.*—About 33 days at temperatures of 23° C.

*Root description.*—Fine; white in color.

*Rooting habit.*—Freely branching; dense.

Plant description:

*Plant and growth habit.*—Low mounding and outwardly spreading. Freely branching; about seven lateral branches per plant; pinching is not required, but will enhance lateral branch development; numerous secondary branches develop. Moderate to vigorous growth habit. Rapid growth rate.

*Plant height.*—About 18 cm.

*Plant diameter.*—About 34 cm by 42 cm.

Lateral branch description:

*Length.*—About 28 cm.

*Diameter.*—About 3 mm.

*Internode length.*—About 2.3 cm.

*Strength.*—Strong.

*Aspect.*—Initially upright to outwardly arching to nearly horizontal.

*Texture.*—Pubescent; viscid.

*Color.*—146B.

Foliage description:

*Arrangement.*—Before flowering, alternate, simple; after flowering, opposite, simple.

*Length.*—About 4 cm.

*Width.*—About 1.5 cm.

*Shape.*—Elliptic.

*Apex.*—Acute.

*Base.*—Attenuate.

*Margin.*—Entire.

*Texture, upper and lower surfaces.*—Pubescent; viscid.

*Venation pattern.*—Pinnate; arcuate.

*Color.*—Developing foliage, upper surface: 146A. Developing foliage, lower surface: 146B. Fully expanded foliage, upper surface: 147B; venation, 147C. Fully expanded foliage, lower surface: 147C; venation, 147C.

*Petiole.*—Length: About 3 mm. Diameter: About 1 mm. Texture, upper and lower surfaces: Pubescent. Color, upper and lower surfaces: 144C.

Flower description:

*Flower arrangement and habit.*—Salverform flowers arranged singly arising from leaf axils. Freely flowering habit with usually about twelve open flowers and flower buds per lateral branch at a time. Flowers persistent. Flowers face mostly outwardly.

*Fragrance.*—Faint; sweet and spicy.

*Natural flowering season.*—Plants of the new *Petunia* initiate and develop flowers about four weeks after planting. Flowering commences naturally during the spring and plants flower continuously throughout the summer.

*Flower longevity.*—Individual flowers last about four to five days on the plant.

*Flower diameter.*—About 4 cm.

*Flower length* (*height*).—About 4 cm.

*Flower throat diameter.*—About 8 mm.

*Flower tube diameter.*—About 3 mm.

*Flower tube length.*—About 2.2 cm.

*Flower bud.*—Shape: Elongated oblong to obovate. Length: About 2.7 cm. Diameter: About 7 mm. Color: 82C.

*Corolla.*—Arrangement: Five petals fused at the base and opening into a flared trumpet. Petal length from throat: About 1.8 cm. Petal width: About 1.9 cm. Petal shape: Roughly spatulate to obovate. Petal apex: Pointed. Petal margin: Serrate; frilled in appearance. Petal texture, upper and lower surfaces: Smooth, velvety. Tube texture: Pubescent. Color: Petal, when opening, upper surface: 77A. Petal, when opening, lower surface: 75A to 75B. Petal, fully opened, upper surface: 78C to 78D; venation, 78C; color becoming closer to 82C with development; towards the throat, 75D. Petal, fully opened, lower surface: 75D; venation, 195A. Throat: 18C; venation, 195B. Tube (outer surface): 82B; venation, 185B to 185C.

*Calyx.*—Arrangement: One star-shaped calyx tube with five sepals fused at the base per flower. Sepal length: About 1.2 cm. Sepal width: About 1.5 mm. Sepal shape: Linear. Sepal apex: Acute. Sepal margin: Entire. Sepal texture, upper and lower surfaces: Pubescent. Color, upper surface: 146A. Color, lower surface: 146B.

*Peduncles.*—Length: About 1.8 cm. Diameter: About 1 mm. Angle: About 45° from vertical. Strength: Strong. Texture: Pubescent. Color: 146B.

*Reproductive organs.*—Stamens: Quantity/arrangement: Five per flower. Anther shape: Oval. Anther length: About 2 mm. Anther color: 155A. Pollen amount: Moderate. Pollen color: 155A. Pistils: Quantity: One per flower. Pistil length: About 1.5 cm. Style length: About 1.2 cm. Style color:

145D. Stigma shape: Anvil-shaped. Stigma color: 145B. Ovary color: 144A. Seed/fruit: Seed and fruit development have not been observed on plants of the new *Petunia*.

Temperature tolerance: Plants of the new *Petunia* have been observed to tolerate temperatures from about 10° C. to about 38° C.

Pathogen/pest resistance: Plants of the new *Petunia* have not been observed to be resistant to pests and pathogens common to *Petunia*.

It is claimed:

1. A new and distinct *Petunia* plant named 'Blue Frill Pink' as illustrated and described.

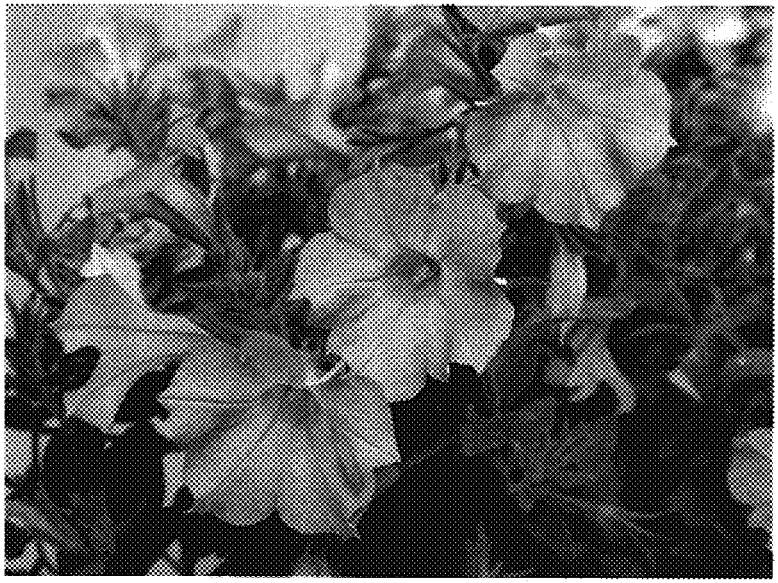
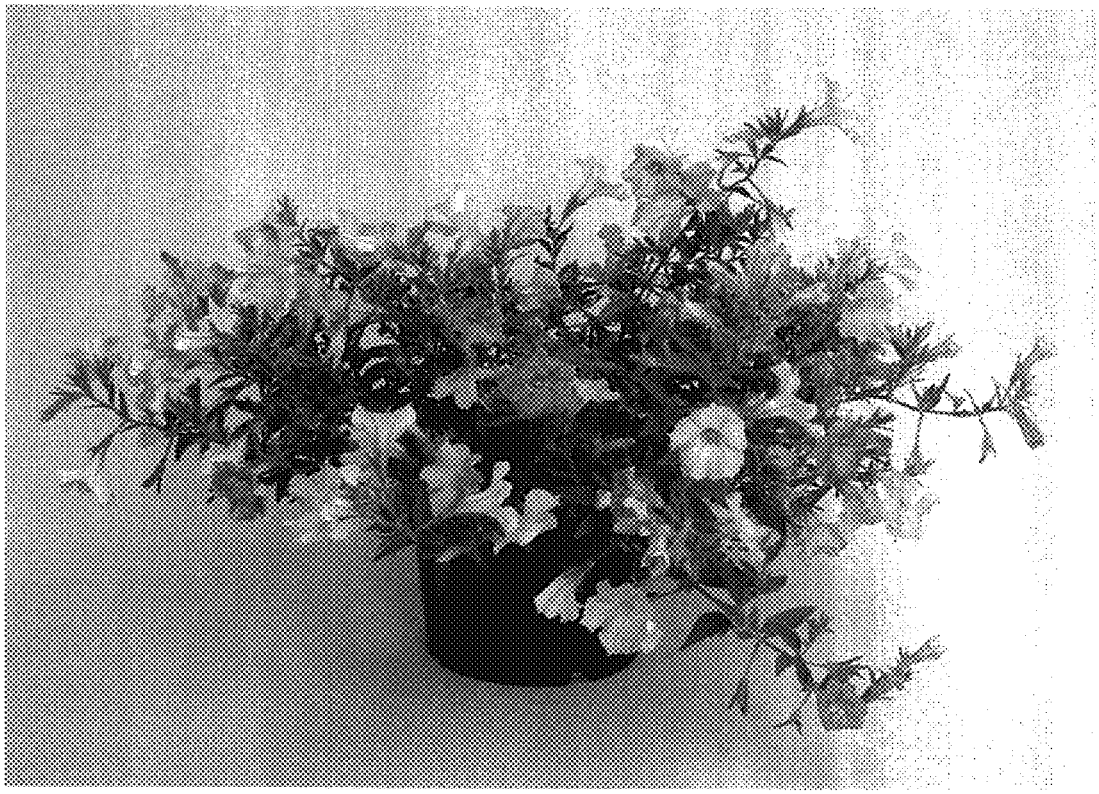

* * * * *